(12) United States Patent
Mogna et al.

(10) Patent No.: US 9,233,130 B2
(45) Date of Patent: Jan. 12, 2016

(54) PROBIOTIC BACTERIA BASED COMPOSITION AND USE THEREOF IN THE PREVENTION AND/OR TREATMENT OF RESPIRATORY PATHOLOGIES AND/OR INFECTIONS AND IN THE IMPROVEMENT OF THE INTESTINAL FUNCTIONALITY

(75) Inventors: Giovanni Mogna, Novara (IT); Gian Paolo Strozzi, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 1750 days.

(21) Appl. No.: 11/719,027

(22) PCT Filed: Oct. 5, 2005

(86) PCT No.: PCT/IB2005/003214
§ 371 (c)(1),
(2), (4) Date: May 10, 2007

(87) PCT Pub. No.: WO2006/054135
PCT Pub. Date: May 26, 2006

(65) Prior Publication Data
US 2008/0107634 A1 May 8, 2008

(30) Foreign Application Priority Data
Nov. 16, 2004 (IT) .............................. MI2004A2189

(51) Int. Cl.
*A61K 9/14* (2006.01)
*A61K 35/741* (2015.01)
*A61K 35/744* (2015.01)
*A61K 35/745* (2015.01)
*A61K 35/747* (2015.01)

(52) U.S. Cl.
CPC ............... *A61K 35/747* (2013.01); *A61K 9/145* (2013.01); *A61K 35/741* (2013.01); *A61K 35/744* (2013.01); *A61K 35/745* (2013.01)

(58) Field of Classification Search
CPC . A61K 2300/00; A61K 31/43; A61K 31/431; A61K 2039/5256; A61K 35/74; A61K 35/744; A61K 35/768; A61K 39/00; A61K 48/00; A61K 31/10; A61K 31/437; A61K 45/06; A61K 9/0014; C07K 16/30; C07K 16/40; C12N 15/86; C12N 2710/24
See application file for complete search history.

(56) References Cited

U.S. PATENT DOCUMENTS

| | | |
|---|---|---|
| 6,241,983 B1 | 6/2001 | Paul et al. |
| 6,379,663 B1 | 4/2002 | Gill et al. |
| 2002/0031503 A1 | 3/2002 | Gill et al. |
| 2003/0180260 A1 | 9/2003 | Clancy et al. |
| 2003/0180272 A1 | 9/2003 | Isolauri et al. |
| 2004/0062758 A1* | 4/2004 | Mayra-Makinen et al. .......... 424/93.45 |
| 2004/0126872 A1 | 7/2004 | Rehberger et al. |
| 2005/0074442 A1 | 4/2005 | Ranganathan |
| 2006/0013806 A1 | 1/2006 | Isolauri et al. |
| 2008/0107634 A1 | 5/2008 | Mogna et al. |
| 2011/0027243 A1 | 2/2011 | Mogna et al. |

FOREIGN PATENT DOCUMENTS

| | | |
|---|---|---|
| DE | 202 02 562 U1 | 5/2002 |
| EP | 1 195 095 | 4/2002 |
| EP | 1 773 361 | 9/2012 |
| EP | 2 219 658 | 8/2013 |
| JP | 10-167972 A | 6/1998 |
| WO | 9910476 A1 | 3/1999 |
| WO | 0197821 A1 | 12/2001 |
| WO | 03071883 A1 | 9/2003 |
| WO | 2006/013588 | 2/2006 |
| WO | 2006/054135 | 5/2006 |
| WO | 2007/125558 | 11/2007 |

OTHER PUBLICATIONS

H.M. Timmerman et al., "Monostrain, multistrain and multispecies probiotics—A comparison of functionality and efficacy", International Journal of Food Microbiology, Elsevier Science Publishers, Amsterdam, NL, ISSN: 0168-1605, vol. 96, No. 3, Nov. 15, 2004, pp. 219-233, XP004580747.
Hatakka, et al., "Effect of Long Term Consumption of Probiotic Milk on Infections in Children Attending Day Care Centres: Double Blind, Randomized Trial", BMJ (online), vol. 322, No. 7298, Jun. 2, 2001, pp. 1-5—http://www.bmj.com/content/322/7298.1327.full.pdf.
Tomasik, et al., "Probiotics and Prebiotics", Cereal Chemistry, Mar. 2003, vol. 80, No. 2, pp. 113-117.
Zago, M. et al. "Characterization and probiotic potential of *Lactobacillus plantarum* strains isolated from cheeses" Abstract only *Food Microbiology* vol. 28, Issue 5, Aug. 2011, pp. 1033-1040.
Douillard, F.P. et al. "Comparative Genomic and Functional Analysis of 100 *Lactobacillus rhamnosus* Strains and Their Comparison with Strain GG" *PLOS Genetics* vol. 9, Issue 8, Aug. 2013, pp. 1-15.
Pregliasco, F. et al. "A New Chance of Preventing Winter Diseases by the Administration of Synbiotic Formulations" *J. Clin Gastroenterol* vol. 42, Supp. 3, Part 2, Sep. 2008, pp. S224-S233.
International Search Report mailed on May 12, 2009 for PCT/EP2008/066700 filed on Dec. 3, 2008 in the name of Probiotical S.P.A.
International Search Report mailed on Feb. 16, 2006 for PCT/EP2005/003214 filed on Mar. 26, 2005 in the name of BASF Aktingesellschaft—German with English translation.

(Continued)

*Primary Examiner* — Debbie K Ware
(74) *Attorney, Agent, or Firm* — Steinfl & Bruno LLP

(57) ABSTRACT

The object of the present invention is a probiotic bacteria based composition and use thereof in the prevention and/or treatment of respiratory pathologies and/or infections and in the contemporaneous improvement of the intestinal functionality, which can be compromised by therapeutic treatments adopted for re-solving said pathological conditions. Besides that, aim of this invention is a probiotic bacteria-based composition comprising moreover a suitable quantity of at least a substance or nourishment having prebiotic properties and eventually, of suitable pharmacologically active substances.

22 Claims, No Drawings

(56) References Cited

OTHER PUBLICATIONS

Final Office Action mailed on Nov. 7, 2014 for U.S. Appl. No. 12/745,441, filed Oct. 22, 2010 in the name of Giovanni Mogna et al.
Non-Final Office Action mailed on Mar. 26, 2013 for U.S. Appl. No. 12/745,441, filed Oct. 22, 2010 in the name of Giovanni Mogna et al.
Non-Final Office Action mailed on Sep. 21, 2012 for U.S. Appl. No. 12/745,441, filed Oct. 22, 2010 in the name of Giovanni Mogna et al.
Restriction Requirement mailed on Jul. 31, 2012 for U.S. Appl. No. 12/745,441, filed Oct. 22, 2010 in the name of Giovanni Mogna et al.
Written Opinion mailed on May 12, 2009 for PCT/EP2008/066700 filed on Dec. 3, 2008 in the name of Probiotical S.P.A.
Written Opinion mailed on Feb. 16, 2006 for PCT/EP2005/003214 filed on Mar. 26, 2005 in the name of BASF Aktingesellschaft—German with English translation.

* cited by examiner

PROBIOTIC BACTERIA BASED COMPOSITION AND USE THEREOF IN THE PREVENTION AND/OR TREATMENT OF RESPIRATORY PATHOLOGIES AND/OR INFECTIONS AND IN THE IMPROVEMENT OF THE INTESTINAL FUNCTIONALITY

The present invention relates to probiotic bacteria based compositions, if necessary integrated with pre-biotic substances, and the use thereof in the prevention and/or treatment of respiratory pathologies and/or infections and in the contemporaneous improvement of the intestinal functionality, which may result compromised from therapeutic treatments adopted for resolving said pathological conditions.

In the last fifty years, the employ in the food field of probiotic bacteria has gained an always increasing importance.

For "probiotic" it is understood to mean those living species-specific microorganisms which, when swallowed or applied in a sufficient number, are able to induce in the consumer specific functional and beneficial effects on the state of health of the host.

If the action of the probiotic microorganism plays a pharmacologically active role towards pathological forms concerning the host, the probiotic microorganism can be defined by the term "biotherapeutic agent", to testify the potential ability of supplying a valid help to the medical therapy.

Therefore, considering that the beneficial properties of the probiotics can be both of a general systemic order and aimed to solve specific disorders or diseases, their use concerns various applicative fields, from the food industry to the pharmaceutical one.

In the pharmaceutical field, the probiotic bacteria are usually employed, for example, in the prevention and treatment of intestinal pathologies of a different origin and nature.

The possible beneficial action of the probiotic bacteria is also object of study, for example in patients suffering from diabetes mellitus of type 2, chronic autoimmune and inflammatory pathologies, tumor pathologies, high serum levels of cholesterol.

However, the use of probiotic bacteria in the prevention and/or therapeutic treatment of the respiratory pathologies is not known.

In particular, the use of probiotic bacteria, in association, or not, with opportune substances having pre-biotic properties for the prevention and/or treatment of respiratory pathologies and/or infections and, at the same time, for the improvement and/or the regularization of the intestinal functionality, which can result compromised (indeed, very often it results compromised) by therapeutic treatments adopted for resolving said pathological conditions, is not known. Usually, the respiratory pathologies and/or infections are treated by using the administration, sometimes also massive and for prolonged times, of antibiotics and/or antiinflammatories.

Unfortunately, the side effects caused by the use of these drugs are often troublesome, harmful and weakening for the organism.

The object of the present invention is to prevent and/or therapeutically treat respiratory pathologies and/or infections of a various origin and nature, without causing undesired side effects, such as those induced by the traditional treatments with antibiotics and/or antiinflammatories.

Another of the objects of the present invention is to prevent and/or therapeutically treat respiratory pathologies and/or infections of a various origin and nature, by simultaneously improving and/or regularizing the intestinal functionality of the organism, often compromised by said pathological conditions.

These and other objects, which will better result from the following detailed description, have been attained by the Applicant, which has unexpectedly found that a composition including an opportune mixture of probiotic bacteria is able to give an adequate response to the problems above-pointed out.

An object of the present invention is therefore the use of a composition including a mixture of probiotic bacteria for the preparation of a medicament for the prevention and/or the therapeutic treatment of respiratory pathologies and/or infections, as summarized in the appended independent claim.

Another object of the present invention is a composition for the use above-mentioned, including a mixture of probiotic bacteria, belonging to the genus *Lactobacillus* and/or genus *Bifidobacterium*, whose features are summarized in the appended independent claim.

A kit for the co-ordinated administration of said composition in combination with one or more pharmacologically active substances, as summarized in the appended independent claim, forms then a further object of the present invention.

Preferred embodiments of the present invention are summarized in the appended dependent claims.

In a preferred embodiment, the composition of the present invention is used for the preparation of a medicament for the prevention and/or the therapeutic treatment of respiratory pathologies and/or infections.

In another preferred embodiment, the composition of the present invention is used for the preparation of a medicament for the prevention and/or the therapeutic treatment of respiratory pathologies and/or infections, with a simultaneous improvement and/or regularization of the intestinal functionality of the organism.

In another preferred embodiment, the composition of the present invention is used for the preparation of an influenza vaccine.

In a further preferred embodiment, the composition of the present invention includes a mixture of three probiotic bacterial species, belonging to the genus *Lactobacillus* and the genus *Bifidobacterium*.

In a further preferred embodiment, the composition of the present invention additionally includes at least a substance having prebiotic properties.

By the term "prebiotic", are generally shown substances or components of the diet (such as, for example, fibres), neither digestible nor absorbable by the organism, which, when arrived integral in the colon, selectively stimulate the development and the activity of the microbial groups beneficial for the health of the individual.

The association of probiotics with prebiotic sub-stances or foods gives rise to compositions generally shown by the term "symbiotic".

In another preferred embodiment, said composition additionally includes at least another probiotic bacterium.

In an additional preferred embodiment, said composition further includes at least a pharmacologically active substance.

The compositions of the present invention proved useful preferably for the prevention and/or treatment of the following pathologies:

influenza like syndromes, often characterized by fever and affections at the expense of the respiratory system (usually shown in the art with the ILI abbreviation, that is Influenza Like Illness);

bronchitic pathologies of a different nature (including those of a chronic type);

pathologies concerning the high respiratory tree, such as for example, laryngitis and tracheitis (generally shown in the art by the URTI abbreviation, that is Upper Respiratory Tract Infections);

common cold;

cough.

The compositions of the present invention include at least a probiotic bacterial species.

Preferably, said compositions include a mixture of multiple bacterial probiotic species.

More preferably, said probiotic bacterial species are opportunely selected among those belonging to the genus *Lactobacillus* and/or genus *Bifidobacterium*.

In a particularly preferred embodiment, said compositions include a mixture consisting of the following three bacterial species: *Bifidobacterium lactis, Lactobacillus casei* subsp. *rhamnosus, Lactobacillus plantarum*.

Advantageously, particularly preferred bacterial strains belonging to said mixture of three bacterial species are resulted those selected from:

*Bifidobacterium lactis*, ID n. LMG P-21384 (deposited to the Belgian Coordinated Collections of Microorganisms—BCCM LMG Collection, on Jan. 31, 2002);

*Lactobacillus casei* subsp. *rhamnosus*, ID n. DSM 16605 (deposited to the DSMZ—Deutsche Sammlung von Mikroorganismen und Zellkulturen GmbH, Braunsweig, Germany, on Jul. 20, 2004);

*Lactobacillus plantarum*, ID n. LMG P-21021 (deposited to the Belgian Coordinated Collections of Microorganisms—BCCM LMG Collection, on Oct. 16, 2002);

*Lactobacillus plantarum*, ID n. LMG P-21020 (deposited to the Belgian Coordinated Collections of Microorganisms—BCCM LMG Collection, on Oct. 16, 2002);

*Lactobacillus plantarum*, ID n. LMG P-21022 (deposited to the Belgian Coordinated Collections of Microorganisms—BCCM LMG Collection, on Oct. 16, 2002);

*Lactobacillus plantarum*, ID n. LMG P-21023 (deposited to the Belgian Coordinated Collections of Microorganisms—BCCM LMG Collection, on Oct. 16, 2002).

In another particularly preferred embodiment, the compositions of the present invention further include at least a substance having prebiotic properties.

Said prebiotic preferably includes carbohydrates which are not digested and absorbed by the organism.

Said carbohydrates are preferably selected from: fructo-oligosaccharides (or FOS), short-chain fructo-oligosaccharides, inulin, isomalt-oligosaccharides, pectins, galacto-oligosaccharides (or GOS), arabinogalactan, xylo-oligosaccharides (or XOS), chitosan-oligosaccharides (or COS), glucanmannan, beta-glucans, Konjac, guar, arabic, xanthan gums, modified and resistant starches, polydextrose, D-tagatose.

Particularly preferred prebiotics are the short-chain fructo-oligosaccharides (for simplicity shown hereinbelow as FOSs-c.c.); said FOSs-c.c. are not digestable glucides, generally obtained by the conversion of the beet sugar and including a saccharose molecule to which three glucose molecules are bonded.

In another particularly preferred embodiment, the compositions of the present invention further include, in addition to the characterizing mixture, consisting of the three bacterial species above-defined, at least another probiotic bacterium.

Preferably, said additional probiotic is selected among the following bacterial species:

*Bifidobacterium adolescentis, Bifidobacterium angulatum, Bifidobacterium animalis, Bifidobacterium bifidum, Bifidobacterium breve, Bifidobacterium catenulatum, Bifidobacterium denticolens, Bifidobacterium dentium, Bifidobacterium gallicum, Bifidobacterium infantis, Bifidobacterium inopinatum, Bifidobacterium longum, Bifidobacterium pseudocatenulatum, Enterococcus faecium, Lactobacillus acidophilus, Lactobacillus casei, Lactobacillus casei* subsp. *paracasei, Lactobacillus delbrueckii* subsp. *bulgaricus, Lactobacillus fermentum, Lactobacillus GG, Lactobacillus pentosus, Lactobacillus salivarius, Saccharomyces boulardi, Streptococcus thermophilus, Lactococcus lactis* subsp. *lactis, Lactococcus lactis* subsp. *diacetylactis*.

Additional particularly preferred bacterial strains belonging to said probiotic bacterial species are those selected from:

*Lactobacillus acidophilus*, ID n. LMG P-21381 (deposited to the Belgian Coordinated Collections of Microorganisms—BCCM LMG Collection, on Jan. 31, 2002);

*Lactobacillus casei* subsp. *paracasei*, ID n. LMG P-21380 (deposited to the Belgian Coordinated Collections of Microorganisms—BCCM LMG Collection, on Jan. 31, 2002);

*Lactobacillus pentosus*, ID n. LMG P-21019 (deposited to the Belgian Coordinated Collections of Microorganisms—BCCM LMG Collection, on Oct. 16, 2002);

*Lactobacillus delbrueckii* subsp. *bulgaricus*, ID n. DSM 16607 (deposited to the DSMZ—Deutsche Sammlung von Mikroorganismen und Zellkulturen GmbH, Braunsweig, Germany, on Jul. 20, 2004);

*Lactobacillus delbrueckii* subsp. *bulgaricus*, ID n. DSM 16606 (deposited to the DSMZ—Deutsche Sammlung von Mikroorganismen und Zellkulturen GmbH, Braunsweig, Germany, on Jul. 20, 2004).

In another particularly preferred embodiment, the compositions of the present invention further include at least a pharmacologically active substance, so as to be able to perform a combined action to that exerted by said active substances.

Advantageously, such associations are revealed synergic, accordingly allowing the use of relatively low doses of pharmaceutical active substance, with a considerable decrease of the possible side effects induced by the administration of the drug alone.

Preferred pharmacologically active substances are, for example, selected from:

antibiotics, antiinflammatories, immunomodulatings, mucolytics, antispasmodics, vitamins.

The composition of the invention are preferably formulated in admixture with appropriate excipients, such as carriers, lubricants, dispersers, flavourings, sweeteners, stabilizers, preservatives, antioxidants, additives, such as amino acids, vitamins, enzymes, generally used in the formulation and the pharmaceutical art.

By mere way of absolutely non limiting example, among the particularly preferred excipients and additives there may be mentioned starch, tween, fragrances, such as those of mandarin, grapefruit, strawberry, bilberry, all fruits, saccharose, glucose, acesulfame, aspartame, ascorbic acid, parabens, glutamine, arginine, superoxide dismutase, glutathione.

Particularly preferred compositions of the present invention are those for oral administration.

Typical preferred embodiments are, for example, capsules, beads, solutions or suspensions ready to drink, powders or granulates sachets (to be suspended or dissolved in water or non-carbonated and non-alcoholic beverages at the time of use) or similar forms, tablets, effervescent formulations.

The compositions of the prevent invention can also be formulated in a coated, lacquered, encapsulated or microencapsulated form, so as to be gastroresistant.

Said composition can also be formulated in a controlled-release form, so as to selectively release the active substances in the intestinal tract, particularly in the colon.

Among the preferred embodiments of the present invention, there may be mentioned those formulations wherein the preferred bacterial strains of the invention are preferably used in a freeze-dried form.

The freeze-drying of said strains, alone or in admixture with opportune excipients, is carried out by using techniques and equipments generally employed in the freeze-drying processes of pharmaceutical and/or food compositions.

The compositions of the present invention are prepared in a traditional way by using, depending on the type of formulation that one wishes to prepare, preparative techniques known to the skilled in the pharmaceutical sector.

By way of absolutely non limiting example, a granular formulation, to be suspended or dissolved in water at the time of use, will be prepared by intimately mixing the components of the composition (active substances, co-adjuvants, excipients), reducing them to the desired granulometry and moisture degree, before packing them in single dose sealed sachets.

In turn, a controlled-release composition will be, for example, prepared by microencapsulating or microcoating the microgranulated mixture of the substances constituting the formulation with opportune mixtures of biocompatible polymers (such as, for example, Eudragit of different type and structure) resistant to the gastric juices of the stomach and able to release said components after a proper residence time in the gastrointestinal tract, or at pH values typical of the colon.

The microencapsulated mixture thus obtained will be, for example, used for the preparation of tablets, capsules or beads, depending on the selected commercial kind of presentation.

As for the dosage, the bacterial species constituting the mixture of probiotic bacteria characterizing the present invention are present in a mutual weight ratio between 0.1:10 to 10:1, preferably in a mutual weight ratio between 0.5:1 to 2:1, more preferably in a mutual weight ratio of about 1:1.

In the particularly preferred case wherein said mixture of probiotic bacteria consists of the three bacterial species *Bifidobacterium lactis, Lactobacillus casei* subsp. *Rhamnosus, Lactobacillus plantarum*, said bacterial species are preferably present in a weight ratio of 1:1:1.

The additional probiotic, if any, is present in a weight ratio between 0:1 to 100:1, with respect to the total quantitative of the bacterial species of said mixture; preferably, in a weight ratio between 2:1 to 15:1; more preferably, from 5:1 to 10:1.

The additional probiotic, if any, is present in a weight ratio between 0:1 to 10:1, with respect to the total quantity of the bacterial species of said mixture; preferably, in a weight ratio from 0.5:1 to 3:1. Each single bacterial species of said mixture of probiotic bacteria of the present invention is present in a concentration between $1 \cdot 10^6$ UFC/dose to $1 \cdot 10^{12}$ UFC/dose; preferably, from $1 \cdot 10^9$ UFC/dose to $1 \cdot 10^{11}$ UFC/dose.

In a particularly preferred embodiment of the invention, a granulate for oral use, packed in single dose sachets to be dissolved in water before the intake is prepared.

By way of absolutely non limiting example, some preferred compositions of the invention are given hereinbelow.

Composition A

In a single dose sachet, 5 g of granulate for oral use are introduced, containing:

a)—0.1 g of *Bifidobacterium lactis* ID n. LMG P-21384, at a concentration of $1 \cdot 10^{11}$ CFU/g of bacterial strain, equal to $2 \cdot 10^9$ CFU/g of composition;

b)—0.1 g of *Lactobacillus casei* subsp. *rhamnosus* ID n. DSM 16605, at a concentration of $1 \cdot 10^{11}$ CFU/g of bacterial strain, equal to $2 \cdot 10^9$ CFU/g of composition;

c)—0.1 g of *Lactobacillus plantarum* ID n. LMG P-21020, at a concentration of $1 \cdot 10^{11}$ CFU/g of bacterial strain, equal to $2 \cdot 10^9$ CFU/g of composition;

d)—FOS-c.c.: 3 g;

e)—glucose: 1.7 g.

Composition B

In a single dose sachet, 5 g of granulate for oral use are introduced, containing:

a)—0.5 g of *Bifidobacterium lactis* ID n. LMG P-21384, at a concentration of $1 \cdot 10^{12}$ CFU/g of bacterial strain, equal to $1 \cdot 10^{11}$ CFU/g of composition;

b)—0.2 g of *Lactobacillus casei* subsp. *rhamnosus* ID n. DSM 16605, at a concentration of $1 \cdot 10^{11}$ CFU/g of bacterial strain, equal to $4 \cdot 10^9$ CFU/g of composition;

c)—0.1 g of *Lactobacillus plantarum* ID n. LMG P-21022, at a concentration of $1 \cdot 10^{11}$ CFU/g of bacterial strain, equal to $2 \cdot 10^9$ CFU/g of composition;

d)—FOS-c.c.: 4 g;

e)—acesulfame: 0.2 g.

Composition C

In a single dose sachet, 5 g of granulate for oral use are introduced, containing:

a)—0.2 g of *Bifidobacterium lactis* ID n. LMG P-21384, at a concentration of $1 \cdot 10^{11}$ CFU/g of bacterial strain, equal to $4 \cdot 10^9$ CFU/g of composition;

b)—0.2 g of *Lactobacillus casei* subsp. *rhamnosus* ID n. DSM 16605; at a concentration of $1 \cdot 10^{11}$ CFU/g of bacterial strain, equal to $4 \cdot 10^9$ CFU/g of composition;

c)—0.1 g of *Lactobacillus plantarum* ID n. LMG P-21023, at a concentration of $1 \cdot 10^{12}$ CFU/g of bacterial strain, equal to $2 \cdot 10^{10}$ CFU/g of composition;

d)—FOS-c.c.: 3.5 g;

e)—0.5 g of *Lactobacillus delbrueckii* subsp. *bulgaricus* ID n. DSM 16607, at a concentration of $1 \cdot 10^7$ CFU/g of bacterial strain, equal to $1 \cdot 10^6$ CFU/g of composition;

f)—acesulfame: 0.2 g;

g)—vitamin C: 0.3 g.

In another preferred embodiment, the pharmaceutical compositions of the present invention may also contain one or more pharmacologically active substances.

Said pharmacologically active substances can opportunely be formulated in admixture with the other components of the composition, such that they can be taken with a single administration.

Said pharmacologically active substances can also be formulated in a discrete packages, so as to allow an independent administration (if necessary also in different times) of the components, however such that the synergic effect is maintained, depending on the requirements of the patient.

In this case, independent packages are arranged, containing the composition of the present invention and the pharmacologically active substance/s, respectively.

The discrete packages above-mentioned are then introduced in a proper kit for allowing the patient to sequentially or separately take them, so as to benefit of a opportunely coordinated therapy depending on its own requirements.

By mere way of example, a kit as the one above-mentioned can contain a number of sachets, or capsules, for the oral administration of the compositions of the present invention, in combination with a proper number of doses of antibiotic and/or multivitaminic complex and/or mucolytic, sufficient for a week of therapy.

By way of absolutely non limiting example, in support of the wide application potential of the present invention, the results of a clinical study carried out with one of the preferred compositions of the same are shown hereinbelow.

In a perspective study, conduced in double-blind randomized against placebo, the ability of the composition A of the present invention of improving the organism protection and restoring a normal state of health thereof towards the respiratory infections has been evaluated.

The rational of the clinical trial carried out consists in that the medical literature data show the association existing between the predisposition to the influenza like seasonal infections at the expense of the respiratory system (ILI and ARI) and the presence of an insufficient mucosal immunity.

In particular, what observed during the years is an increase of the pathologies above-mentioned in those subjects that, for some reasons (such as for example physical stress, chronic pathologies, ageing) had a low protection from the mucosal immunity.

The study has involved the enrolment of 237 subjects, of which 122 treated with the preparation A and 115 treated with placebo.

The mean age of the two different samples was 35.8 (with standard deviation 15.3 years) and 34.1 (with standard deviation 16.3 years).

To each patient of the first group, the intake per os of the sachet content of granulate of preparation A (by previous dissolution in water or other kind of non-carbonated nor alcoholic beverage) has been prescribed, each morning for 30 consecutive days.

To the placebo group, the intake of the content of a sachet containing 5 g of glucose has been prescribed (with the same administration forms and posology).

The course of the health condition of the enrolled subjects has been followed through the drawing up of a daily diary, in which those attending the study (or the sanitary staff put in charge of the control) have reported the daily presence of pathologies at the expense of the respiratory system (for the month of treatment or the two following months).

Incidence, length and subjective gravity of the acute respiratory infections, as well as the course of the intestinal functionality have been examined.

For the comparison between the frequencies of events between the two groups, the chi-square test with the Yates' correction has been used, while those relating to length and gravity of the cases found between the groups the ANOVA (ANalysis Of VAriance) has been used, except for the case of non homogeneity of the variances (evaluated through the Bartlett's test), where it has been substituted by the Kruskall-Wallis's test. For the statistical analysis, the "Epi Info" programme, version 6.04d has been used.

At the same time as the execution of the main trial, the validity of the defense provided to the organism by the symbiotic composition A has been evaluated on another group of subjects, in good health and without any pathologies at the expense of the respiratory system.

On said subjects, the qualitative and quantitative, dosage of the secretion at the mucosal level of the secretory IgA has been carried out, before, during and for 30 days after the administration of the composition A.

The experimentation has pointed out a statistically significant decrease of the length of the conditions generally considered (−1.32 days; p=0.016) and, in particular, for those due to infections of the high respiratory tracts (URTI; −2.83 days; p=0.034).

It has also been found a reduction trend for the other considered pathologies categories, such as bronchitis, influenza, common cold, cough.

The analytical determination of the secretory IgA in the salivary samples of the subjects treated with the composition A has pointed out an increasing production of the IgAs starting from the $5^{th}$-$6^{th}$ day from the beginning of the treatment, increase which has lasted up to about 4-14 days from the suspension of the same. This data confirms the effectiveness of the symbiotic composition A for increasing the systemic immune defenses and of the mucous of the respiratory system, condition which, among other things, allows to prevent and fight infections caused by influenza and parainfluenza virus.

Also the inspection relating to the intestinal functionality (compromised by the pathologies abovementioned) which, following to the intake of the symbiotic composition has shown an improvement is revealed statistically significant, both in terms of reduction of the swelling and in terms of the regularity of the intestine.

These inspections point out as the regular prolonged intake of a symbiotic pharmaceutical composition according to the present invention is able to affect in a positive way the health of the organism, both in a preventive function and in a therapeutic function, towards the respiratory pathologies and/or infections.

With respect, in particular, to the preventive aspect, it is possible to state that the regular intake of a symbiotic pharmaceutical composition according to the present invention is able to effectively protect the organism from the onset of the pathologies above-mentioned in competition with a traditional influenza vaccine, however without inducing the negative symptoms (for example generalized discomforts, intermittent occasional fever, pain in the bones and articulations and allergic reactions).

Accordingly, the symbiotic compositions of the present invention can also be used for the preparation of a medicament acting as an influenza vaccine.

Furthermore, it has also been pointed out that the intake of a pharmaceutical composition according to the present invention is simultaneously able to improve and/or regularize the intestinal functionality of the organism, often compromised by said pathologies.

The invention claimed is:

1. A method for preventing a respiratory pathology and/or infection in a human patient, or for therapeutically treating respiratory pathologies with simultaneous improving and/or regularizing the intestinal functionality of an organism compromised by the respiratory pathologies, the method comprising a step of
administering to the patient a therapeutically effective amount of a composition comprising a mixture of probiotic bacteria and a carrier, the mixture consisting of the following three bacteria species: *Bifidobacterium lactis, Lactobacillus casei* subsp. *rhamnosus, Lactobacillus plantarum*.

2. The method according to claim 1, wherein the three bacteria are selected from the group consisting of:
*Bifidobacterium lactis*, ID n. LMG P-21384;
*Lactobacillus casei* ssp. *rhamnosus*, ID n. DSM 16605;
*Lactobacillus plantarum*, ID n. LMG P-21021;
*Lactobacillus plantarum*, ID n. LMG P-21020;
*Lactobacillus plantarum*, ID n. LMG P-21022; and
*Lactobacillus plantarum*, ID n. LMG P-21023.

3. The method according to claim 1, wherein said composition further includes at least a prebiotic selected from the group consisting of: fructo-oligosaccharides, short chain fructo-oligosaccharides, inulin, isomalto-oligosaccharides, pectins, galacto-oligosaccharides, arabinogalactan, xylo-oligosaccharides, chitosan-oligosaccharides, glucanmannan, betaglucans, Konjac, guar, arabic, xanthan gums, modified and resistant starches, polydextrose, and D-tagatose.

4. The method according to claim 1, wherein said composition further includes at least a probiotic bacteria selected from the group consisting of:
Bifidobacterium adolescentis, Bifidobacterium angulatum, Bifidobacterium animalis, Bifidobacterium bifidum, Bifidobacterium breve, Bifidobacterium catenulatum, Bifidobacterium denticolens, Bifidobacterium dentium, Bifidobacterium gallicum, Bifidobacterium infantis, Bifidobacterium inopinatum, Bifidobacterium longum, Bifidobacterium pseudocatenulatum, Enterococcus faecium, Lactobacillus acidophilus, Lactobacillus casei, Lactobacillus casei ssp. paracasei, Lactobacillus delbrueckii ssp. bulgaricus, Lactobacillus fermentum, Lactobacillus GG, Lactobacillus pentosus, Lactobacillus salivarius, Saccharomyces boulardi, Streptococcus thermophilus, Lactococcus lactis ssp. lactis, and Lactococcus lactis ssp. diacetylactis.

5. The method according to claim 4, wherein said probiotic bacteria is selected from the group consisting of:
Lactobacillus acidophilus, ID n. LMG P-21381;
Lactobacillus casei ssp. Paracasei, ID n. LMG P-21380;
Lactobacillus pentosus, ID n. LMG P-21019;
Lactobacillus delbrueckii ssp. bulgaricus, ID n. DSM 16607; and
Lactobacillus delbrueckii ssp. bulgaricus, ID n. DSM 16606.

6. The method according to claim 1, wherein said composition further includes at least a pharmacologically active substance, said pharmacologically active substance being directly present in admixture with the other components of said composition or being formulated and packaged separately from the same.

7. The method of claim 1, wherein said respiratory pathology and/or infection is selected from the group consisting of influenza, influenza like illness, bronchitis, bronchitic pathologies, upper respiratory tract infections, common cold, and cough.

8. The method of claim 1, wherein said respiratory pathology and/or infection is upper respiratory tract infections.

9. The method of claim 1, wherein said respiratory pathology and/or infection is bronchitis.

10. The method of claim 1, wherein said respiratory pathology and/or infection is influenza.

11. The method of claim 1, wherein said respiratory pathology and/or infection is common cold.

12. The method of claim 1, wherein said respiratory pathology and/or infection is cough.

13. A composition comprising a mixture of the following three bacteria: Bifidobacterium lactis, Lactobacillus casei ssp. rhamnosus, and Lactobacillus plantarum and a carrier, wherein the three bacteria are selected from the group consisting of: Bifidobacterium lactis, ID n. LMG P-21384; Lactobacillus casei ssp. rhamnosus, ID n. DSM 16605; Lactobacillus plantarum, ID n. LMG P-21021; Lactobacillus plantarum, ID n. LMG P-21020; Lactobacillus plantarum, ID n. LMG P-21022; and Lactobacillus plantarum, ID n. LMG P-21023.

14. The composition according to claim 13, wherein said composition further includes at least a prebiotic selected from the group consisting of: fructo-oligosaccharides, short chain fructo-oligosaccharides, inulin, isomalto-oligosaccharides, pectins, galacto-oligosaccharides, arabinogalactan, xylo-oligosaccharides, chitosan-oligosaccharides, glucanmannan, beta-glucans, Konjac, guar, arabic, xanthan gums, modified and resistant starches, polydextrose, and D-tagatose.

15. The composition according to claim 14, wherein said prebiotic is present in a weight ratio between 0:1 to 100:1, based on the total quantity of said three bacteria.

16. The composition according to claim 13, wherein said composition further includes at least a probiotic bacteria selected from the group consisting of:
Bifidobacterium adolescentis, Bifidobacterium angulatum, Bifidobacterium animalis, Bifidobacterium bifidum, Bifidobacterium breve, Bifidobacterium catenulatum, Bifidobacterium denticolens, Bifidobacterium dentium, Bifidobacterium gallicum, Bifidobacterium infantis, Bifidobacterium inopinatum, Bifidobacterium longum, Bifidobacterium pseudocatenulatum, Enterococcus faecium, Lactobacillus acidophilus, Lactobacillus casei, Lactobacillus casei ssp. paracasei, Lactobacillus delbrueckii ssp. bulgaricus, Lactobacillus fermentum, Lactobacillus GG, Lactobacillus pentosus, Lactobacillus salivarius, Saccharomyces boulardi, Streptococcus thermophilus, Lactococcus lactis ssp. lactis, and Lactococcus lactis ssp. diacetylactis.

17. The composition according to claim 16, wherein said probiotic bacteria is selected from the group consisting of:
Lactobacillus acidophilus, ID n. LMG P-21381;
Lactobacillus casei ssp. paracasei, ID n. LMG P-21380;
Lactobacillus pentosus, ID n. LMG P-21019;
Lactobacillus delbrueckii ssp. bulgaricus, ID n. DSM 16607; and
Lactobacillus delbrueckii ssp. bulgaricus, ID n. DSM 16606.

18. The composition according to claim 13, wherein said composition further includes at least a pharmacologically active substance, said pharmacologically active substance being directly present in admixture with the other components of said composition, or being formulated and packaged separately from the same.

19. The composition according to claim 13, wherein said three bacteria of said mixture are present in a weight ratio between 0.1:1 to 10:1.

20. The composition according to claim 13, wherein each bacteria is dosed in a quantity between $1 \cdot 10^6$ UFC/dose to $1 \cdot 10^{12}$ UFC/dose.

21. The composition according to claim 13, including a granulate for oral use, containing:
a) 0.1 g of said Bifidobacterium lactis ID n. LMG P-21384, at a concentration of $1 \cdot 10^{11}$ CFU/g of the bacteria, equal to $2 \cdot 10^9$ CFU/g of the composition;
b) 0.1 g of said Lactobacillus casei ssp. rhamnosus ID n. DSM 16605, at a concentration of $1 \cdot 10^{11}$ CFU/g of the bacteria, equal to $2 \cdot 10^9$ CFU/g of the composition;
c) 0.1 g of said Lactobacillus plantarum ID n. LMG P-21020, at a concentration of $1 \cdot 10^{11}$ CFU/g of the bacteria, equal to $2 \cdot 10^9$ CFU/g of the composition;
d) FOS-c.c.: 3 g; and
e) glucose: 1.7 g.

22. A kit including, as components:
at least a composition according to claim 13; and
at least a pharmacologically active substance;
separately packaged, for an independent administration of said components.

* * * * *